US009737666B2

(12) United States Patent
Nzike et al.

(10) Patent No.: US 9,737,666 B2
(45) Date of Patent: Aug. 22, 2017

(54) ASSEMBLY FOR A DRUG DELIVERY DEVICE AND DRUG DELIVERY DEVICE

(75) Inventors: Philippe Nzike, Frankfurt am Main (DE); Steffen Raab, Frankfurt am Main (DE); Uwe Dasbach, Frankfurt am Main (DE); Uwe Boeser, Frankfurt am Main (DE); Ulrich Bruggemann, Frankfurt am Main (DE); Brice Ulrich Tchouadje, legal representative, Hessen (DE); Kevin Igor Youmbi Ngatchou, legal representative, Hessen (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 769 days.

(21) Appl. No.: 13/504,296

(22) PCT Filed: Nov. 1, 2010

(86) PCT No.: PCT/EP2010/066552
§ 371 (c)(1),
(2), (4) Date: Nov. 1, 2012

(87) PCT Pub. No.: WO2011/054775
PCT Pub. Date: May 12, 2011

(65) Prior Publication Data
US 2013/0046247 A1 Feb. 21, 2013

(30) Foreign Application Priority Data
Nov. 3, 2009 (EP) .................... 09174962

(51) Int. Cl.
*A61M 5/315* (2006.01)
*A61M 5/24* (2006.01)
(52) U.S. Cl.
CPC .......... *A61M 5/31535* (2013.01); *A61M 5/24* (2013.01); *A61M 5/31555* (2013.01);
(Continued)

(58) Field of Classification Search
CPC ............ A61M 2005/2407; A61M 5/24; A61M 5/31535; A61M 5/31555; A61M 5/31556; A61M 5/31585
(Continued)

(56) References Cited

U.S. PATENT DOCUMENTS 533,575 A 2/1895 Wilkens
5,226,895 A 7/1993 Harris
(Continued)

FOREIGN PATENT DOCUMENTS

CN 101184519 A 5/2008
CN 100434631 C 11/2008
(Continued)

OTHER PUBLICATIONS

International Preliminary Report on Patentability for Int. App. No. PCT/EP2010/066552, mailed May 18, 2012.
(Continued)

*Primary Examiner* — Imani Hayman
(74) *Attorney, Agent, or Firm* — McDonnell Boehnen Hulbert & Berghoff LLP

(57) ABSTRACT

An assembly for a drug delivery device is disclosed. An example assembly includes a housing, a rotation member, a drive member, and at least one correction member. The rotation member is adapted to be rotated with respect to the housing in a first rotational direction for delivering a dose of a drug. The drive member is coupleable to the rotation member for delivering the dose. In a delivery mode, the drive member and the rotation member are coupled such that the drive member follows rotational movement of the rotation member in the first rotational direction due to mechanical interaction of the rotation member and the drive member. In a correction mode, the rotation member and the drive member are decoupled such that the rotation member is
(Continued)

Figure 1:
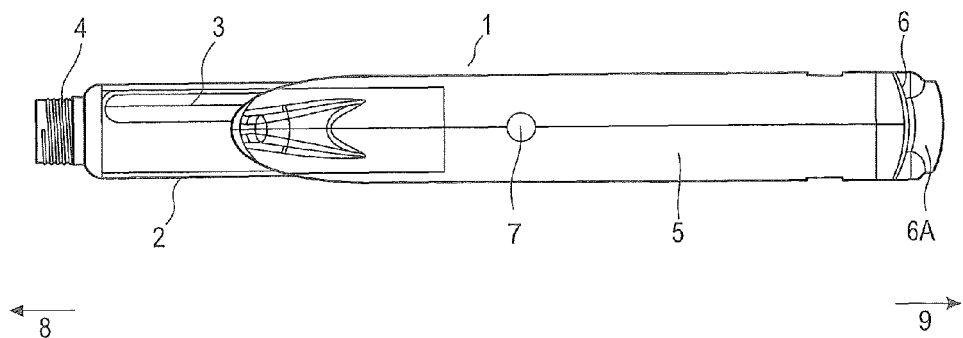

rotatable in the first rotational direction with respect to the drive member.

17 Claims, 2 Drawing Sheets

(52) U.S. Cl.
CPC .... *A61M 5/31556* (2013.01); *A61M 5/31585* (2013.01); *A61M 2005/2407* (2013.01); *A61M 2205/581* (2013.01); *A61M 2205/582* (2013.01)

(58) Field of Classification Search
USPC .................................................. 604/207–211
See application file for complete search history.

(56) References Cited

U.S. PATENT DOCUMENTS

| | | | |
|---|---|---|---|
| 5,279,586 | A | 1/1994 | Balkwill |
| 5,304,152 | A | 4/1994 | Sams |
| 5,320,609 | A | 6/1994 | Haber et al. |
| 5,383,865 | A | 1/1995 | Michel |
| 5,480,387 | A | 1/1996 | Gabriel et al. |
| 5,505,704 | A | 4/1996 | Pawelka et al. |
| 5,582,598 | A | 12/1996 | Chanoch |
| 5,626,566 | A | 5/1997 | Petersen et al. |
| 5,674,204 | A | 10/1997 | Chanoch |
| 5,688,251 | A | 11/1997 | Chanoch |
| 5,827,232 | A | 10/1998 | Chanoch et al. |
| 5,921,966 | A | 7/1999 | Bendek et al. |
| 5,961,495 | A | 10/1999 | Walters et al. |
| 6,004,297 | A | 12/1999 | Steenfeldt-Jensen et al. |
| 6,193,698 | B1 | 2/2001 | Kirchhofer et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,899,698 | B2 | 5/2005 | Sams |
| 6,936,032 | B1 | 8/2005 | Bush, Jr. et al. |
| 7,241,278 | B2 | 7/2007 | Moller |
| 7,695,454 | B2 | 4/2010 | Barron et al. |
| 9,114,211 | B2 | 8/2015 | Enggaard et al. |
| 2002/0052578 | A1 | 5/2002 | Moller |
| 2002/0120235 | A1 | 8/2002 | Enggaard |
| 2003/0050609 | A1 | 3/2003 | Sams |
| 2004/0059299 | A1 | 3/2004 | Moller |
| 2004/0210199 | A1 | 10/2004 | Atterbury et al. |
| 2004/0236285 | A1 | 11/2004 | Fisher et al. |
| 2004/0267207 | A1 | 12/2004 | Veasey et al. |
| 2005/0033244 | A1* | 2/2005 | Veasey et al. ................ 604/211 |
| 2005/0113765 | A1 | 5/2005 | Veasey et al. |
| 2006/0153693 | A1* | 7/2006 | Fiechter ............ A61M 5/31553 417/63 |
| 2007/0197976 | A1 | 8/2007 | Jacobs et al. |
| 2009/0275916 | A1 | 11/2009 | Harms et al. |
| 2010/0114037 | A1 | 5/2010 | Moser et al. |

FOREIGN PATENT DOCUMENTS

| | | |
|---|---|---|
| CN | 100464795 C | 3/2009 |
| DE | 102007026555 A1 | 12/2008 |
| EP | 0295075 | 12/1988 |
| EP | 0295075 A1 | 12/1988 |
| EP | 0615762 | 9/1994 |
| EP | 0937471 | 8/1999 |
| EP | 0937476 | 8/1999 |
| EP | 1974761 A2 | 10/2008 |
| JP | H06-296691 | 10/1994 |
| JP | 2004-535255 | 11/2004 |
| WO | 93/07922 | 4/1993 |
| WO | 9307922 A1 | 4/1993 |
| WO | 99/38554 | 8/1999 |
| WO | 01/10484 | 2/2001 |
| WO | 03/008023 | 1/2003 |
| WO | 2006/128794 | 12/2006 |
| WO | 2006128794 A2 | 12/2006 |
| WO | 2008031238 A1 | 3/2008 |
| WO | 2008/128373 | 10/2008 |
| WO | 2008128373 A1 | 10/2008 |
| WO | 2009/062685 | 5/2009 |

OTHER PUBLICATIONS

Extended European Search Report issued in European Patent Application No. 09174962.2 dated May 6, 2010.
Form PCT/IB/326, Notification of Transmittal of the International Search Report and the Written Opinion of the International Searching Authority, or the Declaration dated May 12, 2011.
First Chinese Office Action issued in Chinese Patent Application No. 201080060425.1 dated Jul. 18, 2013.
Patent Examination Report No. 1 issued in Australian Patent Application No. 2010314169 dated Mar. 30, 2014.
Communication pursuant to Article 94(3) EPC issued in European Patent Application No. 10775794.0 dated Oct. 14, 2015.

* cited by examiner

ASSEMBLY FOR A DRUG DELIVERY DEVICE AND DRUG DELIVERY DEVICE

CROSS REFERENCE TO RELATED APPLICATIONS

The present application is a 35 U.S.C. 371 National Application of PCT/EP2010/066552 filed Nov. 1, 2010, which claims priority to European Patent Application No. 09174962.2, filed Nov. 3, 2009, the entire contents of which are incorporated entirely herein by reference.

This disclosure relates to an assembly for a drug delivery device and a drug delivery device incorporating such an assembly.

In a drug delivery device a bung within a cartridge that contains a drug may be provided. The bung may be displaced with respect to the cartridge for delivering a set dose of the drug from the cartridge. In general, it is desirable that the delivered dose of the drug matches the dose which was previously set by a user, i.e. the dose accuracy should be high. Furthermore, it is desirable that an incorrectly set dose of the drug can be adjusted, in particular corrected, by the user such that the dose of the drug dispensed afterwards matches exactly the desired dose.

Drug delivery devices are described in documents WO 2008/031238 A1 and US 2007/0197976 A1, for example.

It is an object of the present disclosure to provide an assembly facilitating provision of a novel, preferably an improved, drug delivery device.

This object may be achieved by the subject matter of the independent claim. Further features and advantageous embodiments are the subject matter of the dependent claims.

According to one aspect an assembly for a drug delivery device is provided. The assembly may comprise a housing. The assembly may comprise a rotation member. The rotation member may be adapted to be rotated with respect to the housing in a first rotational direction for delivering a dose of a drug. The first rotational direction may be counter-clockwise, for example. The assembly may comprise a drive member. The drive member may be, preferably releasably, coupleable to the rotation member for delivering the dose. The assembly may comprise at least one correction member. In a delivery mode, the drive member and the rotation member are expediently coupled such that the drive member follows rotational movement of the rotation member in the first rotational direction due to mechanical interaction of the rotation member and the drive member, e.g. the rotation member and the drive member may be rotationally locked. In the delivery mode, the rotation member and, hence, the drive member may rotate about a common rotation axis. The rotation axis may be a main longitudinal axis of the housing. In a correction mode, the rotation member and the drive member are expediently decoupled such that the rotation member is rotatable in the first rotational direction with respect to the drive member. In the correction mode, the rotation member and the drive member are expediently rotationally unlocked. For switching from the delivery mode into the correction mode, the correction member may be movable, preferably radially inwardly, with respect to the housing. The assembly may be configured such that movement, preferably radial inward movement, of the correction member with respect to the housing is converted into a relative movement, preferably a relative axial movement, between the drive member and the rotation member for decoupling the drive member and the rotation member.

A further aspect relates to a drug delivery device. The drug delivery device expediently comprises the assembly described above. The drug delivery device may comprise a cartridge. The cartridge may hold a plurality of doses of a drug. The assembly may provide a dose correction mechanism. The dose correction mechanism may allow for correcting a set dose of the drug.

The dose correction mechanism expediently enables correction of a previously, in particular not correctly, set dose of the drug without drug being dispensed from the cartridge during the correction action. In this way, provision of an easily handled, user-friendly drug delivery device providing high dose accuracy is facilitated.

For switching into the correction mode, the user may push onto the correction member, thereby displacing the correction member with respect to the housing. The, preferably radial inward, movement of the correction member may be converted into axial movement of the rotation member and the drive member relatively to each other and with respect to the housing. Relative movement of the rotation member and the drive member may comprise axial movement of the drive member with respect to the rotation member. In this case, the rotation member may be stationary with respect to the housing. Additionally or alternatively, relative movement of the rotation member and the drive member may comprise axial movement of the rotation member with respect to the drive member. In this case, the drive member may be stationary with respect to the housing.

Due to said relative decoupling movement the rotation member and drive member may be decoupled, e.g. disengaged. In particular, the drive member and the rotation member are no longer rotationally locked due to the relative movement of the rotation member and the drive member. When the rotation member and the drive member are decoupled, the device may be in the correction mode. The set dose of the drug can now easily be corrected. Rotational movement of the drive member is prevented. In this way, a user-friendly drug delivery device is achieved.

According to an embodiment, in a setting mode, the rotation member is adapted to be rotated in a second rotational direction with respect to the drive member for setting a dose of a drug. The second rotational direction may be opposite to the first rotational direction. The second rotational direction may be clockwise, for example. In the delivery mode and/or in the setting mode, the drive member and the rotation member may be coupled to one another, e.g. engaged, by means of a uni-directional friction clutch mechanism, for example a slipping clutch. The friction clutch mechanism may be configured to prevent relative rotational movement of the rotation member and the drive member during rotation of the rotation member in the first rotational direction, e.g. in the delivery mode. The friction clutch mechanism may be configured to permit relative rotational movement between the rotation member and the drive member during rotation of the rotation member in the second rotational direction, e.g. in the setting mode.

In the setting mode, the rotation member and the drive member are expediently coupled, in particular engaged, by means of the uni-directional friction clutch mechanism. However, the drive member may be prevented from following rotation of the rotation member in the second rotational direction. This may help to increase dose accuracy.

In the delivery mode, the rotation member and the drive member may also be coupled, in particular engaged, by means of the uni-directional friction clutch mechanism. The drive member may follow rotation of the rotation member in the first rotational direction due to mechanical cooperation of the drive member and the rotation member for delivering the set dose.

In the correction mode, the rotation member may again rotate in the first rotational direction. However, in the correction mode, the rotation member and the drive member are expediently decoupled, in particular disengaged, and, hence, the drive member may be prevented from following rotation of the rotation member in the first rotational direction. Hence, in the correction mode, the rotation member may rotate in the first rotational direction without movement of the drive member. In this way, correction of a not correctly set dose of the drug is facilitated.

According to an embodiment, a stop member is provided. The drive member and the stop member are coupled, preferably permanently coupled, to one another by an other uni-directional friction clutch mechanism, for example a slipping clutch. The friction clutch mechanism is expediently configured to permit relative rotational movement between the stop member and the drive member during rotation of the rotation member in the first rotational direction, e.g. in the delivery mode. The clutch mechanism may be configured to prevent relative rotational movement between the drive member and the stop member during rotation of the rotation member in the second rotational direction, e.g. in the setting mode.

Due to mechanical cooperation of the stop member and the drive member, movement, in particular rotation, of the drive member is prevented when setting the dose. This may help to increase dose accuracy.

According to an embodiment, a piston rod is provided. The drive member and the piston rod may be rotationally locked with each other.

The piston rod may be configured to displace the bung with respect to the cartridge for expelling the set dose of the drug from the cartridge. Preferably, the piston rod is splined to the drive member. In particular, rotational movement of the drive member in the first rotational direction may be converted into movement of the piston rod with respect to the housing due to the splined connection of the drive member and the piston rod.

In the setting mode, the drive member is prevented from rotating with respect to the housing due to mechanical cooperation with the stop member. In the correction mode, the drive member is prevented from rotating with respect to the housing due to decoupling, in particular disengagement, of the drive member and the rotation member. Consequently, in the setting mode and in the correction mode, movement of the piston rod is prevented due to the splined connection of the piston rod and the drive member. In this way, dose accuracy may be increased.

According to an embodiment, for switching into the correction mode, the drive member and the rotation member are moved relatively to each other and with respect to the piston rod for decoupling the rotation member and the drive member. When the drive member is moved with respect to the rotation member, the stop member is expediently moved together with the drive member.

According to an embodiment, in the delivery mode and in the setting mode, the rotation member and/or the stop member is held in abutment, preferably permanent abutment, with the drive member by a force provided by a resilient member. Preferably, the resilient member is a spring member, for example a helical coil spring. The resilient member may exert a force onto the stop member, the drive member and the rotation member when setting, correcting and delivering the dose. Preferably, the force is exerted along the rotation axis. Preferably, the rotation axis runs along a main direction of extent of the piston rod.

According to an embodiment, for switching into the correction mode, a correction force must be applied, said force acting against the force exerted by the resilient member.

The correction force must be applied against the force exerted by the resilient member in order to move the rotation member and the drive member relatively to each other for decoupling the drive member and the rotation member. The correction force is expediently exerted along the rotation axis and preferably in the opposite direction compared to the force exerted by the resilient member. If the correction force is no longer exerted, e.g. after the correction has been completed, the rotation member and the drive member may be brought re-coupled automatically by the resilient member. In this way, automatic switch from the correction mode into the delivery and/or setting mode is facilitated. Thus, a user-friendly drug delivery device is achieved.

According to an embodiment, at least one of the drive member and the rotation member comprises at least one interaction element. For switching into the correction mode, the correction member may mechanically interact with the interaction element. Movement of the correction member may be converted into relative movement between the drive member and the rotation member by mechanical interaction of the correction member and the interaction element.

If relative movement between the drive member and the rotation member comprises movement of the drive member with respect to the rotation member, the interaction element may be part of or fixed to the drive member. Additionally or alternatively, if the rotation member is moved with respect to the drive member for decoupling the drive member and the rotation member, the interaction element may be part of or may be fixed to the rotation member. Preferably, the interaction element is unitarily formed with the drive member and/or the rotation member.

According to an embodiment, the interaction element has an oblique outer face. The outer face may be oblique with respect to the main longitudinal axis of the housing. The outer face may run circumferentially around the interaction element. The correction member may exert a radially, preferably radially inwardly, directed force onto the interaction element for switching into the correction mode. The force may be converted into an axially directed force, e.g. the correction force, by mechanical cooperation of the correction member and the oblique outer face.

According to an embodiment, the correction member is secured against rotational movement with respect to the housing. The correction member may be secured against movement along the main longitudinal axis of the housing. The correction member and the interaction element expediently axially overlap, in particular when the rotation member is coupled to the drive member, e.g. in the setting mode and in the delivery mode.

Preferably, the correction member is secured to the housing such that radial movement of the correction member with respect to the main longitudinal axis of the housing is allowed while rotational movement and movement along the main longitudinal axis of the housing is expediently prevented. Preferably, the correction member is a switch correction button.

According to an embodiment, the correction member is externally actuatable.

In this way, provision of a user-friendly drug delivery device is facilitated enabling an easy and quick correction of an incorrectly set dose of the drug.

According to an embodiment, the correction member is a resilient member or a resiliently mounted member.

Preferably, the correction member comprises or is embodied as a deformable, in particular an elastically deformable, member. In this way, automatic switching from the correction mode back into the delivery mode may be enabled once the correction member is released, for example, due to the restoring force which may move the correction member back into the initial position.

According to an embodiment, two equally configured correction members may be provided. The correction members may be disposed oppositely.

Preferably, the correction members are arranged such that a user can easily push onto the correction members using only two fingers for switching into the correction mode. Thus, provision of an easily handled drug delivery device is facilitated.

According to a preferred embodiment, an assembly for a drug delivery device is provided. The assembly comprises a housing. The assembly comprises a rotation member, the rotation member being adapted to be rotated with respect to the housing in a first rotational direction for delivering a dose of a drug. The assembly comprises a drive member, the drive member being coupleable to the rotation member for delivering the dose. The assembly comprises at least one correction member. In a delivery mode, the drive member and the rotation member are coupled such that the drive member follows rotational movement of the rotation member in the first rotational direction due to mechanical interaction of the rotation member and the drive member. In a correction mode, the rotation member and the drive member are decoupled such that the rotation member is rotatable in the first rotational direction with respect to the drive member. For switching from the delivery mode into the correction mode, the correction member is movable with respect to the housing, wherein the assembly is configured such that movement of the correction member with respect to the housing is converted into a relative movement between the drive member and the rotation member for decoupling the drive member and the rotation member.

In this way, correction of a previously, in particular not correctly, set dose of the drug is facilitated. Thus, an easily handled and user-friendly drug delivery device is achieved.

Of course, features described above in connection with different aspects and embodiments may be combined with each other and with features described below.

Further features and refinements become apparent from the following description of the exemplary embodiments in connection with the accompanying figures.

Figure 2:
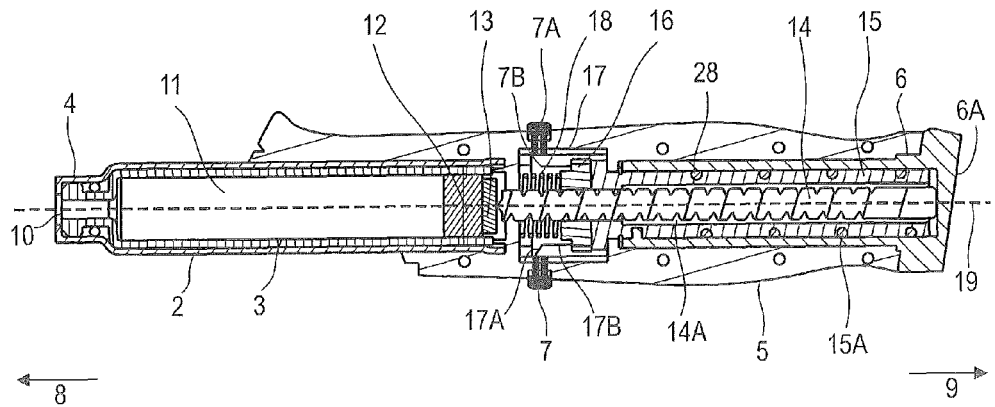
Figure 3:
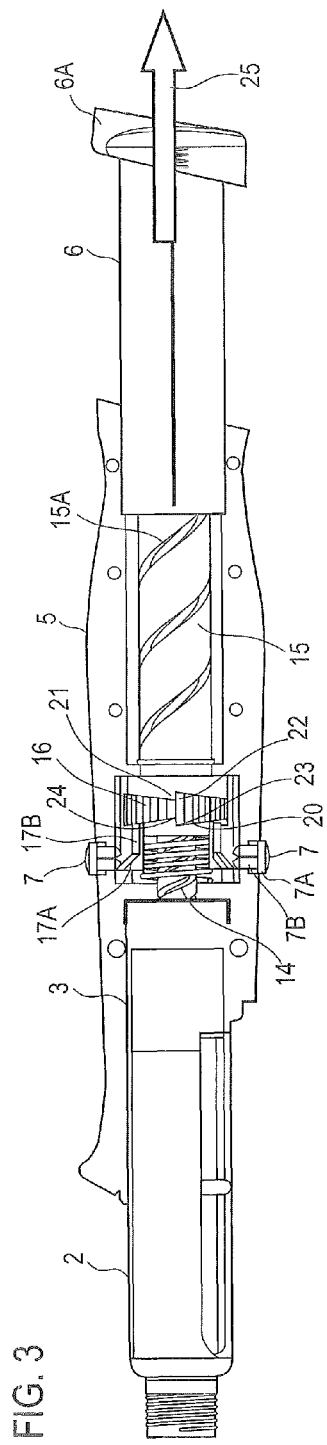
Figure 4:
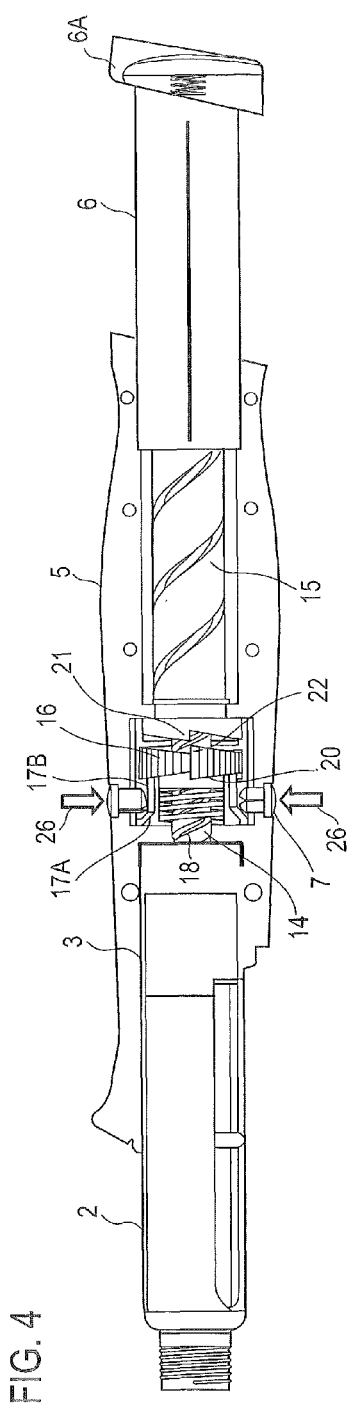
Figure 5:
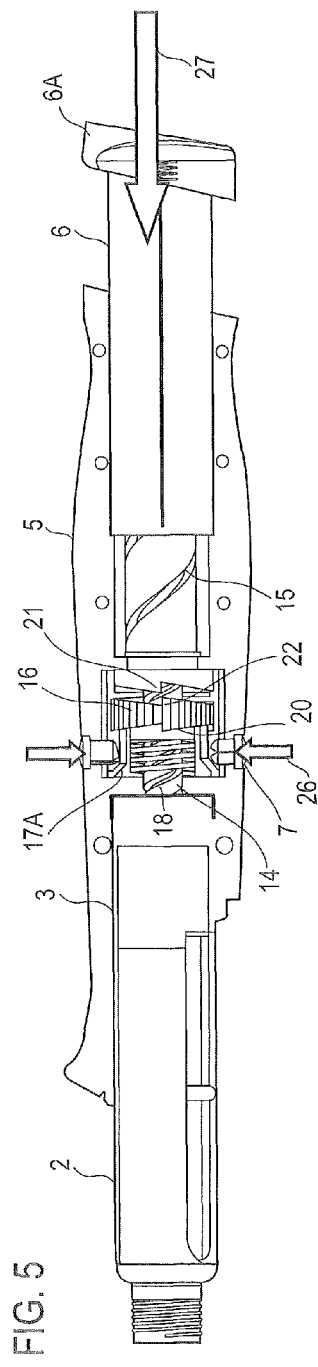

FIG. 1 schematically shows a perspective sectional view of an exemplary embodiment of a drug delivery device, FIG. 2 schematically shows a sectional side view of the drug delivery device of FIG. 1, FIG. 3 schematically shows a perspective sectional view of the drug delivery device shown in FIG. 1 in the setting mode, FIG. 4 schematically shows a perspective sectional view of the drug delivery device of FIG. 3 while switching into the correction mode, and FIG. 5 schematically shows a perspective sectional view of the drug delivery device of FIG. 4 in the correction mode.

Like elements, elements of the same kind and identically acting elements may be provided with the same reference numerals in the figures.

In FIG. 1, a drug delivery device 1 is shown. The drug delivery device 1 comprises a cartridge holder 2. The device 1 comprises a cartridge 3. The cartridge 3 is retained in the cartridge holder 2. The cartridge holder 2 stabilizes the cartridge 3 mechanically.

The cartridge 3 may hold a plurality of doses of a drug (see drug 11, FIG. 2). The drug 11 is preferably a liquid medication, comprising, for example, insulin, like short-acting or long-acting insulin, heparin and/or growth hormones. The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The cartridge 3 has an outlet 10, as shown in FIG. 2. The drug 11 can be dispensed from the cartridge 3 through the outlet 10. The outlet 10 may be covered by a membrane. The membrane may protect the drug 11 against external influences during storage of the cartridge 3.

The drug delivery device 1 may comprise a needle assembly (not explicitly shown), comprising a needle. The needle assembly may be releasably attached to the cartridge holder 2, for example by means of engagement means 4, e.g. a thread. The membrane may be pierced by the needle for dispensing a dose of the drug 11. Alternatively, the drug delivery device 1 may be a needle-free device.

The drug delivery device 1 may be an injection device. The drug delivery device 1 may be a pen-type device, in particular a pen-type injector. The device 1 may be a disposable or a re-usable device. Preferably, the device 1 is configured to dispense variable, preferably user-settable, doses of the drug 11. Alternatively, the device 1 may be a fixed dose device, in particular a device configured to dispensed doses of the drug 11 which may not be varied by the user. The drug delivery device 1 may be a manually, in particular a non-electrically, driven device.

The drug delivery device comprises a housing 5. The drug delivery device 1 and the housing 5 have a distal end and a proximal end. The term "distal end" designates that end of the drug delivery device 1 or a component thereof which is or is to be arranged closest to a dispensing end of the drug delivery device 1. The distal end of the device 1 is indicated by arrow 8. The term "proximal end" designates that end of the device 1 or a component thereof which is or is to be arranged furthest away from the dispensing end of the device 1. The proximal end of the device 1 is indicated by arrow 9.

The housing 5 may be designed to enable a safe and comfortable handling of the drug delivery device 1. The housing 5 may be configured to house, fix, protect or guide inner components of the drug delivery device 1, e.g. components of a drive mechanism, which is described later on in more detail. Preferably, the housing 5 limits or prevents the exposure of the inner components to contaminants such as liquid, dirt or dust. The housing 5 may be a unitary or a multipart component. The housing 5 may comprise a tubular shape, as shown in FIG. 1. Alternatively, the housing 5 may comprise a non-tubular shape.

The cartridge holder 2 and the housing 5 may be, preferably permanently or releasably, secured to one another, for example by a threaded connection. If the cartridge holder 2 is releasably secured to the housing 5, the device 1 may be a re-usable device. In this case, the cartridge holder 2 may be detached from the housing 5 for providing a new cartridge 3, if all of the doses of the drug 11 have already been dispensed. Afterwards, the cartridge holder 2 is re-attached to the housing 5. If the cartridge holder 2 is irreleasably secured to the housing 5 the drug delivery device 1 may be a disposable device.

The drug delivery device 1 comprises a bung 12 (see FIG. 2). The bung 12 may be retained in the cartridge 3. The bung 12 is movable with respect to the cartridge 3. The bung 12 may seal the cartridge 3 proximally. Movement of the bung 12 in the distal direction with respect to the cartridge 3 causes the drug 11 to be dispensed from the cartridge 3 through the outlet 10.

The device 1 comprises a piston rod 14 (see FIG. 2). The piston rod 14 may operate through the housing 5 of the drug delivery device 1. The piston rod 14 may be designed to transfer axial movement through the drug delivery device 1, for example for the purpose of dispensing the drug 11. In particular, the piston rod 14 may be designed to transfer force to the bung 12, thereby pushing the bung 12 in the distal direction with respect to the cartridge 3. In this way, a dose of the drug 11 may be dispensed from the cartridge 3 provided the outlet 10 is open, e.g. after the membrane has been pierced by the needle as described above. The size of the dispensed dose is determined by the distance by which the bung 12 is displaced in the distal direction with respect to the cartridge 3.

The piston rod 14 may be made of a flexible or a rigid material. The piston rod 14 may have a circular or a non-circular cross-section. The piston rod 14 may be a simple rod, a lead-screw, a rack, a pinion system or the like. The piston rod 14 may be of unitary or multipart construction.

A bearing member 13 (see FIG. 2) may be arranged between the bung 12 and the piston rod 14 to advance the bung 12. The bearing member 13 may be displaced together with the piston rod 14 with respect to the housing 5. The piston rod 14 may be rotatable with respect to the bearing member 13. The bearing member 13 may be axially locked to the piston rod 14, for example by means of a snap-fit connection.

The device 1 comprises a drive mechanism. The drive mechanism is arranged within the housing 5 of the drug delivery device 1. The device 1 comprises a dose member 6. The dose member 6 comprises a dose button 6A. The dose member 6 may be part of the drive mechanism. The dose member 6 may be movable with respect to the housing 5. The dose member 6 may be splined to the housing 5. The dose member 6 may be movable in the proximal direction with respect to the housing 5 for setting a dose of the drug 11. The dose member 6 may be movable in the distal direction with respect to the housing 5 for delivering the set dose of the drug 11. Preferably, the dose member 6 is movable in the distal direction with respect to the housing 5 for correcting the set dose, e.g. for reducing the size of the dose or for un-setting the dose, which is explained later on in more detail.

The distance by which the dose member 6 is moved proximally with respect to the housing 5 for setting the dose of the drug 11 may determine the size of the set dose. A proximal end position and a distal end position of the dose member 6 with respect to the housing 5 may be determined by a respective stop feature (not explicitly shown) limiting the proximal or distal movement of the dose member 6 with respect to the housing 5.

The dose button 6A may be configured to be pulled by a user for setting the dose. The dose button 6A may be pushed by the user for dispensing the set and/or corrected dose. The dose button 6A may be part of the dose member 6 or may be connected to the dose member 6.

A force, preferably a user-applied force, causing the dose member 6 to be moved distally with respect to the housing 5 may be transferred to the piston rod 14 by the drive mechanism for dispensing the set dose, which is described later on in more detail. Preferably, the drive mechanism is configured to leave the piston rod 14 stationary with respect to the housing 5 when the dose member 6 is moved in the proximal direction with respect to the housing 5 for setting the dose and in the distal direction with respect to the housing 5 for correcting the set dose.

The drive mechanism comprises a drive member 16. The drive mechanism comprises a rotation member 15. The drive mechanism comprises a stop member 20 (see FIGS. 2 to 5).

The rotation member 15 may be axially displaceable with respect to the housing 5 in a limited fashion, which is described later on in more detail. The rotation member 15 is rotatable with respect to the housing 5. The rotation member 15 may be arranged inside the dose member 6. The dose member 6 may be coupled to, preferably threadedly engaged with, the rotation member 15. For this purpose, the rotation member 15 may comprise outer thread 15A, as shown in FIG. 2. The dose member 6 may comprise a counterpart 28, e.g. a thread (see FIG. 2). The counterpart 28 may be provided within the dose member 6. The dose member 6 and the rotation member 15 may be threadedly engaged such that axial movement of the dose member 6 is expediently converted into rotational movement of the rotation member 15.

Thus, in a setting mode of the device 1, movement of the dose member 6 in the proximal direction with respect to the housing 5 for setting a dose of the drug 11 may be converted into rotation of the rotation member 15 in a second rotational direction with respect to the housing 5. The second rotational direction may be clockwise, for example.

In a delivery mode of the device 1, movement of the dose member 6 in the distal direction with respect to the housing 5 for delivering the set dose may be converted into rotation of the rotation member 15 in a first rotational direction with respect to the housing 5. The first rotational direction may be opposite to the second rotational direction. The first rotational direction may be counter-clockwise and the second rotational direction may be clockwise, for example.

In a correction mode of the device 1, movement of the dose member 6 in the distal direction with respect to the housing 5 for correcting the set dose may be converted into rotation of the rotation member 15 in the first rotational direction with respect to the housing 5.

The drive member 16 may be axially displaceable with respect to the housing 5 in a limited fashion, which is described later on in more detail. The drive member 16 is rotatable with respect to the housing 5. The drive member 16 and the rotation member 15 are preferably configured to rotate about a common rotation axis when delivering the set dose. The rotation axis may be a main longitudinal axis 19 of the housing 5 or the device 1. Preferably, the rotation axis runs along the piston rod 14 and, in particular, along a main direction of extent of the piston rod 14.

The rotation member 15 may be coupled, for example engaged, preferably permanently, to the drive member 16 when the device 1 is in the setting mode. The rotation member 15 may be coupled, preferably permanently, to the drive member 16 when the device 1 is in the delivery mode. However, the rotation member 15 and the drive member 16 are preferably decoupled, in particular disengaged, when the device 1 is in the correction mode, e.g. for correcting an erroneously set dose of the drug 11, which is described later on in more detail.

In the setting mode and in the delivery mode, the rotation member 15 is coupled to the drive member 16 by a uni-directional clutch mechanism, in particular a friction clutch mechanism, for example a slipping clutch. The clutch mechanism permits rotational movement of the rotation member 15 with respect to the drive member 16 when the rotation member 15 rotates in the second rotational direction with respect to the housing 5, e.g. in the setting mode. The clutch mechanism prevents rotational movement of the rotation member 15 with respect to the drive member 16, when the rotation member 15 rotates in the first rotational direction with respect to the housing 5, e.g. in the delivery mode.

In the setting mode and in the delivery mode, the drive member 16 may be arranged to abut or engage the rotation member 15. For engaging the rotation member 15, the drive member 16 comprises a toothing 22 (see FIG. 3). Toothing 22 may be arranged in the proximal end section of the drive member 16, for example. In addition, the rotation member 15 comprises a toothing 21 (see in FIG. 3). Toothing 21 may be arranged in the distal end section of the rotation member 15, for example. In particular, toothing 21 may be arranged at an end section of the rotation member 15 which faces the drive member 16. Toothing 21 and toothing 22 may be configured to mate with each other. Toothing 21 comprises a plurality of teeth. The teeth of toothing 21 may be disposed along a perimeter of the rotation member 15. The teeth of toothing 22 may be disposed along a perimeter of the drive member 16. Toothing 22 comprises a plurality of teeth. The teeth of the respective toothing 20, 21 may extend along the rotation axis.

A respective tooth of toothing 20, 21 may be ramp-shaped, in particular along an azimuthal direction with respect to the rotation axis. The ramp of the respective tooth is limited in the azimuthal direction by a steep end face of said tooth, e.g. a face of the tooth that runs parallel to the rotation axis. When the steep end faces of two respective teeth of toothing 20 and 21 abut and the rotation member 15 is rotated further in the first rotational direction with respect to the housing 5, the steep sides stay in abutment and, hence, the drive member 16 follows rotation of the rotation member 15.

When the rotation member 15 rotates in the second rotational direction with respect to the housing 5, the ramps of the teeth of toothing 20 and 21 slide along each other and, hence, the rotation member 15 rotates with respect to the drive member 16. Accordingly, the device 1 is in the setting mode. An audible and/or tactile feedback may be given to the user when the next tooth of toothings 20, 21 engage with each other.

The drive member 16 engages the piston rod 14. Preferably, the drive member 16 is splined to the piston rod 14. The splined connection of the drive member 16 and the piston rod 14 prevents relative rotational movement of the drive member 16 with respect to piston rod 14. Hence, the drive member 16 and the piston rod 14 are permanently rotationally locked.

The drive member 16 is configured to transfer force, preferably torque, to the piston rod 14. The force transferred may cause the piston rod 14 to be rotated with respect to the housing 5. Additionally or alternatively, the force transferred may cause the piston rod 14 to be displaced in the distal direction with respect to the housing 5 for delivering the set dose of the drug 11.

The piston rod 14 comprises a thread 14A. The thread 14A may be arranged at an outer surface of the piston rod 14. A counterpart, e.g. a further thread, may be provided inside the housing 5 for a threaded engagement of the housing 5 and piston rod 14. Rotational movement of the piston rod 14 may be converted into axial movement of the piston rod 14 in the distal direction with respect to the housing 5 due to the threaded engagement of the piston rod 14 and the housing 5.

The drive member 16 may be arranged between stop member 20 and rotation member 15. The stop member 20 is configured to prevent rotational movement of the drive member 16 in the second rotational direction with respect to the housing 5 when setting the dose of the drug 11. Consequently, in the setting mode, the rotation member 15 rotates with respect to the drive member 16 and with respect to the stop member 20. The stop member 20 is preferably secured against rotation with respect to the housing 5 or integrally formed with respect to the housing 5. The stop member 20 may be axially displaceable with respect to the housing 5. The stop member 20 may be splined to the housing 5.

The stop member 20 may be coupled to the drive member 16 by means of a further uni-directional clutch mechanism, for example a slipping clutch. The clutch mechanism prevents rotational movement of the drive member 16 with respect to the stop member 20 when the rotation member 15 rotates in the second rotational direction with respect to the housing, e.g. when setting the dose of the drug 11. The clutch mechanism permits rotational movement of the drive member 16 with respect to the stop member 20 when the rotation member 15 rotates in the first rotational direction with respect to the housing 5, e.g. when delivering the set dose of the drug 11.

The stop member 20 may be arranged to abut or engage the drive member 16, preferably when setting, when correcting and when delivering the set dose, e.g. in either operation mode of the device 1. The stop member 20 comprises a toothing 24 (see FIG. 3) at one end section which faces the drive member 16, for example the proximal end section of the stop member 20. The teeth of toothing 24 may be ramp-shaped and may be disposed along a perimeter of the stop member 20.

The drive member 16 comprises a further toothing 23 (see FIG. 3), preferably at the distal end section of the drive member 16. Thereby, toothing 23 and toothing 22 of the drive member 16 are disposed oppositely. Toothing 23 may be configured in accordance with toothing 21 of the rotation member 15. Toothing 23 and toothing 24 may be configured to cooperate for preventing rotation of the drive member 16 with respect to the housing 5 and with respect to the stop member 20 when setting the dose of the drug 11.

As rotation of the drive member 16 in the second rotational direction with respect to the housing 5 is prevented, movement of the piston rod 14 in the proximal direction with respect to the housing 5 as well as rotation of the piston rod 14 in the second rotational direction with respect to the housing 5 during setting of the dose is prevented. This may help to increase dose accuracy.

The drive mechanism further comprises a resilient member 18, for example a spring member. Preferably, resilient member 18 is a helical coil spring. The resilient member 18 provides a force which tends to keep the drive member 16 in permanent mechanical cooperation, e.g. engagement, with the stop member 20 and the rotation member 15, when the device 1 is in the delivery mode, in the correction mode and in the setting mode, e.g. in either operation mode of the device 1. Preferably, the force is exerted along the rotation axis.

The drive member 16, the rotation member 15, the stop member 20 and the dose member 6 may comprise or may be embodied as a sleeve, respectively. The piston rod 14 may be arranged and/or driven through at least one, or more, or all of said sleeves.

The drive member 16 comprises at least one interaction element 17. Preferably, the interaction element 17 is arranged in the distal end section of the drive member 16, as indicated in FIG. 2. The interaction element 17 is provided around the drive member 16. Preferably, the drive member 16 and the interaction element 17 are unitarily formed.

The interaction element 17 comprises a skirt 17B. Skirt 17B may be embodied as or may comprise a ring-like portion, for example. Skirt 17B may extend along the main longitudinal axis 19 of the housing 5. The skirt 17B comprises an oblique outer face 17A. The oblique outer face 17A is preferably arranged in the distal end section of the skirt 17B. The oblique outer face 17A may be oblique with respect to the main longitudinal axis 19 of the housing 5. The oblique outer face 17A may run around the drive member 16, preferably along its whole perimeter, and/or around the main longitudinal axis.

The device 1 comprises at least one correction member 7. Preferably, the device 1 comprises two correction members 7, as indicated in FIG. 2. The correction members 7 may be equally configured. The correction members 7 may be user actuatable, e.g. by pushing onto the correction members 7. The correction members 7 may be disposed oppositely such that the user can easily push onto the correction members 7 with two fingers, e.g. the thumb and index finger. Alternatively, the device 1 comprises three or more correction members 7. Preferably, the correction members 7 comprise or are embodied as switch buttons for switching the device 1 into the correction mode.

The correction members 7 are secured against rotation with respect to the housing 5. The correction members 7 are secured against movement along the main longitudinal axis 19 of the housing 5. However, the correction members 7 may be adapted to be radially movable with respect to the housing 5.

The respective correction member 7 comprises a disc-like portion 7A. The disc-like portion 7A is preferably arranged at an outer surface of the housing 5 such that the user is able to push onto the disc-like portion 7A. Consequently, the respective correction member 7 is externally acuatable, in particular user actuatable. When the respective correction member 7 is released by the user, the device 1 may be automatically switched from the correction mode into the delivery mode or back into the setting mode, for example.

The correction members 7 comprise a protruding portion 7B. Preferably, the disc-like portion 7A and the protruding portion 7B are formed unitarily. The protruding portion 7B protrudes radially inwardly with respect to the housing 5. The protruding portion 7B may comprise a tip arranged at the end of the protruding portion 7B being furthest away from the disc-like portion 7A.

The correction members 7, in particular the protruding portion 7B, are configured to mechanically interact with the interaction element 17, in particular with the oblique outer face 17A, for switching the device 1 into the correction mode. Preferably, the correction members 7 axially overlap with the oblique outer face 17A. Preferably, the axial position of the respective correction member 7 with respect to the housing 5 is defined by that axial position the respective interaction element 17, in particular the oblique outer face 17A, has with respect to the housing 5 when the drive member 16 and the rotation member 15 are coupled with each other. Thus, the respective correction member 7 may mechanically interact with the respective interaction element 17, in particular with the oblique outer face 17A, when the correction member 7 is moved with respect to the housing 5.

Preferably, the correction members 7 are resilient members, in particular elastically deflectable members. Alternatively, the correction members 7 may be resiliently mounted members. In this case, a spring member, for example a coil spring, may be arranged between the disc-like portion 7A and the protruding portion 7B. The spring member may be biased radially inwardly when the correction member 7 is pushed inwardly by the user. The biased spring member may relax radially outwardly, when the disc-like portion 7A is released, e.g. after having corrected the dose, thereby displacing the correction member 7 automatically radially outwardly. In this way, the device 1 may be automatically switched from the correction mode back into the setting mode or into the delivery mode when the respective correction member 7 is released.

For switching into the correction mode (see also FIG. 4), the correction members 7, in particular the disc-like portion 7A, are pushed by the user. Thereby, the correction members 7 are displaced radially inwardly with respect to the housing 5 and towards the oblique outer face 17A. The spring member is thus biased radially inwardly.

When the correction members 7 are displaced radially inwardly, the tip of the protruding portion 7B may abut the oblique outer face 17A. Thereby, the correction members 7 exert a radially inwardly directed force onto the interaction element 17. The radially inwardly directed force is converted into an axially directed force, e.g. a correction force, by mechanical cooperation of the tip of the protruding portion 7B and the oblique outer face 17A, which tip is moved along the oblique outer face 17A.

In particular, the oblique outer face 17A may be adapted to mechanically interact with the correction member 7, in particular with the tip of the protruding portion 7B, such that radial inward movement of the correction member 7 with respect to the housing 5 is converted into distal movement of the drive member 16 and, thus, of the stop member 20, with respect to the housing 5 and with respect to the rotation member 15 (see FIG. 4) for decoupling the drive member 16 and the rotation member 15.

Accordingly, movement of the correction members 7 in the radial inward direction with respect to the housing 5 is converted into a relative (axial) movement between the drive member 16 and the rotation member 15 for decoupling the drive member 16 and the rotation member 15.

When the drive member 16 and, hence, the stop member 20 are displaced distally with respect to the rotation member 15, the user-applied correction force acts against and overcomes the force exerted by the resilient member 18, which tends to hold the rotation member 15 and the stop member 20 in abutment with the drive member 16, as described previously. Consequently, the resilient member 18 is axially biased when the drive member 16 and the stop member 20 are displaced distally with respect to the rotation member 15 for decoupling the drive member 16 and the rotation member 15. When the drive member 16 and, hence, the stop member 20, are moved with respect to the rotation member 15, the stop member 20 and the drive member 16 are held in abutment due to the force exerted by the resilient member 18. Relative movement between the drive member 16 and the rotation member 15, i.e. decoupling movement, may lead to a gap (see FIGS. 4 and 5) between the drive member 16 and the rotation member 15. The gap may have a size such that the toothing 21 of the rotation member 15 and the toothing 22 of the drive member 16 are out of engagement, i.e. the rotation member 15 and the drive member 16 are disengaged. Accordingly, the relative displacement should be greater than or at least equal to the depth of a respective tooth of toothings 20, 21.

When the drive member 16 and the rotation member 15 are decoupled, the drive member 16 and the rotation member 15 are no longer rotationally locked in the first direction. When the drive member 16 and the rotation member 15 are decoupled, the device 1 is in the correction mode (see also FIG. 5). In the correction mode, the rotation member 15 may rotate in the first rotational direction with respect to the drive member 16. Accordingly, the set dose may be corrected without movement of the drive member 16 and, hence, of the piston rod 14.

For switching from the correction mode into the delivery mode or back into the setting mode, the respective correction member 7 may be released. The spring member arranged between the disc-like portion 7A and the protruding portion 7B relaxes radially outwardly. Hence, the respective correction member 7 is automatically displaced radially outwardly such that there is no longer mechanical interaction between the correction member 7 and the interaction element 17. Consequently, the correction force is no longer exerted onto the drive member 16 for keeping the drive member 16 and the rotation member 15 out of engagement.

Thus, the resilient member 18 may relax axially. This may lead to a relative movement between the drive member 16 and the rotation member 15 in the opposite direction as for decoupling, for coupling, in particular engaging, the drive member 16 and the rotation member 15. In particular, the drive member 16 and, hence, the stop member 20 are driven in the proximal direction by the energy which was previously stored within the resilient member 18 during the decoupling.

When the rotation member 15 and the drive member 16 are brought back into engagement, the corrected dose can be delivered or the device 1 may be put away with an unintentionally set dose being unset.

FIG. 3 schematically shows a perspective sectional view of the drug delivery device shown in FIG. 1 in the setting mode.

For setting a dose, the user displaces the dose member 6 in the proximal direction (arrow 25) with respect to the housing 5. To do so, the user may grip dose button 6A and pull it in the proximal direction, for example. Dose member 6 moves proximally also with respect to the rotation member 15.

Proximal displacement of the dose member 6 with respect to the housing 5 is converted into rotational movement of the rotation member 15 in the second rotational direction with respect to the housing 5, in particular on account of the threaded engagement of dose member 6 and rotation member 15. The rotation member 15 also rotates with respect to the drive member 16 and with respect to the stop member 20. An audible and/or tactile feedback may be given to the user when the next tooth of toothing 22 of the drive member 16 is engaged by a respective tooth of toothing 21 of the rotation member 15.

As the piston rod 14 is coupled to the drive member 16 and rotation in the second rotational direction of the drive member 16 would cause the piston rod 14 to be displaced in the proximal direction, the piston rod 14 is prevented from being driven in the proximal direction by interaction of stop member 20 and drive member 16. Dose accuracy can be increased in this way.

The set dose may be visible through a window aperture (not explicitly shown) in the housing 5. When the user realizes that the selected dose is too high or a (fixed) dose was erroneously set, the user may correct the set dose by switching the device 1 into the correction mode.

FIG. 4 schematically shows a perspective sectional view of the drug delivery device of FIG. 3 while switching into the correction mode.

FIG. 5 schematically shows a perspective sectional view of the drug delivery device of FIG. 4 in the correction mode.

When the user wants to correct the previously set dose (see FIG. 3) the user pushes onto the respective correction member 7 (arrow 26) for switching into the correction mode. As described in connection with FIG. 2, radial inward movement of the correction members 7 with respect to the housing 5 is converted into relative decoupling movement of the drive member 16 and the rotation member 15.

When the drive member 16 and the rotation member 15 are decoupled, e.g. when the device 1 is in the correction mode, the dose member 6 can be displaced in the distal direction with respect to the housing 5 for correcting the previously set dose (see arrow 27). The dose member 6 is displaced distally until the desired dose size is reached, which may be displayed in the window aperture (not explicitly shown) of the housing 5, or until the dose is unset.

During the correction movement of the dose member 6, the rotation member 15 rotates in the first rotational direction with respect to the housing 5. As the rotation member 15 and the drive member 16 are decoupled, the drive member 16 is prevented from rotating in the first rotational direction. Accordingly, the piston rod 14, which is driven by the drive member 16, is prevented from movement with respect to the housing 5. In this way, the set dose can easily be corrected and waste of drug 11 may be avoided.

When the dose was corrected, e.g. the desired dose size is displayed in the window aperture, the user may switch the device 1 from the correction mode into the delivery mode by releasing the respective correction member 7. Thereby, the rotation member 15 and the drive member 16 are brought back into engagement, as it was described in connection with FIG. 2. Hence, the rotation member 15 and the drive member 16 are again rotationally locked in the first rotational direction for dispensing the corrected dose.

For dispensing the corrected dose, the dose button 6A is pushed and, hence, the dose member 6 is displaced in the distal direction with respect to the housing 5. The rotation member 15 accordingly rotates in the first rotational direction with respect to the housing 5. The drive member 16 follows rotational movement of the rotation member 15 in the first rotational direction with respect to the stop member 20. An audible and/or tactile feedback may be given to the user when the next tooth of toothing 24 of the stop member 20 is engaged.

Rotational movement of the drive member 16 in the first rotational direction is converted into rotational movement of the piston rod 14 in the first rotational direction. Said movement is converted into movement of the piston rod 14 in the distal direction due to the threaded engagement of the piston rod 14 and the housing 5. Accordingly, the bung 12 is displaced in the distal direction with respect to the cartridge 3 and the corrected dose of the drug 11 is dispensed from the cartridge 3.

As described above, the rotation member 15 and the drive member 16 may be decoupled due to movement of the drive member 16 and, hence, of the stop member 20, with respect to the rotation member 15. Alternatively, in an embodiment not explicitly shown in the drawings, relative movement between the rotation member 15 and the drive member 16 for decoupling the drive member 16 and the rotation member 15 may comprise axial, in particular proximal, movement of the rotation member 15 with respect to the drive member 16 and, in particular, with respect to the stop member 20. In this case, the drive member 16 and the stop member 20 may remain stationary with respect to the housing 5.

When the rotation member 15 is moved relatively to the drive member 16, the interaction element 17 or an additional interaction element may be arranged at the rotation member 15. Accordingly, the oblique outer face 17A may be adapted to mechanically interact with the tip of the protruding portion 7B such that radial inward movement of the correction member 7 with respect to the housing 5 is converted into proximal movement of the rotation member 15 with respect to the drive member 16 and the stop member 20. However, movement of the rotation member 15 with respect to the drive member 16 may cause a movement of the dose member 6 during unsetting or correcting the dose. Movement of the dose member 6 may irritate the user. When the drive member 16 is moved with respect to the rotation member 15, said movement of the dose member 6 may be avoided.

Other implementations are within the scope of the following claims. Elements of different implementations may be combined to form implementations not specifically described herein.

REFERENCE NUMERALS

1 Drug delivery device
2 Cartridge holder
3 Cartridge
4 Engagement means
5 Housing
6A Dose button
6 Dose member
7 Correction member
7A Disc-like portion
7B Protruding portion
8 Distal end
9 Proximal end
10 Outlet
11 Drug
12 Bung
13 Bearing member
14 Piston rod
14A Thread
15 Rotation member
15A Thread
16 Drive member
17 Interaction element
17A Surface
17B Skirt
18 Resilient member
19 Main longitudinal axis
20 Stop member
21 Tooth
22 Tooth
23 Tooth
24 Tooth
25 Arrow
26 Arrow
27 Arrow
28 Counterpart

The invention claimed is:

1. An assembly for a drug delivery device comprising
a housing,
a rotation member, the rotation member being adapted to be rotated with respect to the housing in a first rotational direction for delivering a dose of a drug, and
a drive member, the drive member being coupleable to the rotation member for delivering the dose,
at least one correction member,
wherein, in a delivery mode, the drive member and the rotation member are coupled such that the drive member follows rotational movement of the rotation member in the first rotational direction due to mechanical interaction of the rotation member and the drive member,
and wherein, in a correction mode, the rotation member and the drive member are decoupled such that the rotation member is rotatable in the first rotational direction with respect to the drive member,
wherein, for switching from the delivery mode into the correction mode, the at least one correction member is moveable with respect to the housing, and wherein the assembly is configured such that movement of the at least one correction member with respect to the housing is converted into a relative movement between the drive member and the rotation member for decoupling the drive member and the rotation member.

2. The assembly of claim 1, wherein, in a setting mode, the rotation member is adapted to be rotated in a second rotational direction with respect to the drive member for setting the dose of the drug, and wherein, in the delivery mode and in the setting mode, the drive member and the rotation member are coupled to one another by means of a uni-directional friction clutch mechanism, which is configured to prevent relative rotational movement between the rotation member and the drive member during rotation of the rotation member in the first rotational direction and to permit relative rotational movement between the rotation member and the drive member during rotation of the rotation member in the second rotational direction.

3. The assembly of claim 2, comprising a stop member, wherein the drive member and the stop member are coupled to one another by an other uni-directional friction clutch mechanism, which is configured to permit relative rotational movement between the stop member and the drive member during rotation of the rotation member in the first rotational direction.

4. The assembly of claim 3, wherein the other unidirectional friction clutch mechanism is configured to prevent relative rotational movement between the stop member and the drive member during rotation of the rotation member in the second rotational direction.

5. The assembly of claim 3, wherein, for switching into the correction mode, the drive member and the rotation member are moved relatively to each other and with respect to the piston rod for decoupling the rotation member and the drive member and, wherein, when the drive member is moved with respect to the rotation member, the stop member is moved together with the drive member.

6. The assembly according to claim 3, wherein, in the delivery mode and in the setting mode, the rotation member and the stop member are held in abutment with the drive member by a force provided by a resilient member.

7. The assembly of claim 6, wherein, for switching into the correction mode, a correction force must be applied acting against the force exerted by the resilient member.

8. The assembly according to claim 1, comprising a piston rod, wherein the drive member and the piston rod are rotationally locked with each other.

9. The assembly according to claim 1, wherein at least one of the drive member and the rotation member comprises at least one interaction element, and wherein, for switching into the correction mode, the at least one correction member mechanically interacts with the at least one interaction element to convert movement of the at least one correction member into relative movement between the drive member and the rotation member.

10. The assembly of claim 9, wherein the at least one interaction element has an oblique outer face, and wherein the at least one correction member exerts a radially directed force onto the at least one interaction element, the force being converted into an axially directed force by mechanical cooperation of the at least one correction member and the oblique outer face.

11. The assembly according to claim 9, wherein the at least one correction member is secured against rotational movement with respect to the housing and against movement along a main longitudinal axis of the housing, and wherein the at least one correction member and the at least one interaction element axially overlap.

12. The assembly according to claim 1, wherein the at least one correction member is externally actuatable.

13. The assembly according to claim 1, wherein the at least one correction member is a resilient member or a resiliently mounted member.

14. The assembly according to claim 1, comprising two equally configured correction members, the correction members being oppositely disposed.

15. A drug delivery device comprising the assembly according to claim 1, further comprising a cartridge, the cartridge holding a plurality of doses of a drug, wherein the assembly provides a dose correction mechanism allowing for correcting a set dose.

16. The assembly of claim 1, further comprising a dose member for setting the dose, wherein the at least one correction member is different than the dose member for setting the dose.

17. The assembly of claim 16, wherein, for switching from the delivery mode into the correction mode, the at least one correction member is moveable radially inward with respect to the housing.

* * * * *